United States Patent [19]

Garside et al.

[11] 4,042,697
[45] Aug. 16, 1977

[54] ISOQUINOLIUM COMPOUNDS FOR TREATING DIABETES

[75] Inventors: Peter Garside; Michael John Dimsdale, both of London, England

[73] Assignee: Allen & Hanburys Limited, London, England

[21] Appl. No.: 632,577

[22] Filed: Nov. 17, 1975

Related U.S. Application Data

[63] Continuation of Ser. No. 405,120, Oct. 10, 1973, abandoned.

[30] Foreign Application Priority Data

Oct. 19, 1972 United Kingdom ............... 48211/72

[51] Int. Cl.² ............................................. A61K 31/47
[52] U.S. Cl. ................................. 424/258; 260/286 Q
[58] Field of Search ......................................... 424/258

[56] References Cited

U.S. PATENT DOCUMENTS 3,235,556  2/1966  Wakeman et al. ................... 424/258

Primary Examiner—Frederick E. Waddell
Attorney, Agent, or Firm—Bacon & Thomas

[57] ABSTRACT

Compounds of the general formula 1;

(I)

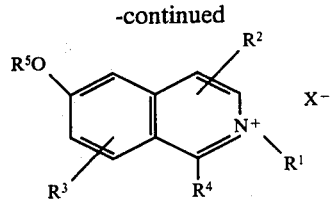

-continued in which
R¹ and R⁵ which may be the same or different represent an alkyl, alkenyl or alkynyl group, which groups may optionally be substituted by an amino, alkylamino or dialkylamino groups, or by hydroxy, alkoxy ($C_{1-4}$), aroyl, aryl or aryloxy groups, in which the aroyl, aryl or aryloxy groups may contain an alkoxy ($C_{1-4}$) substituent; and R⁵ may in addition represent a cycloalkyl group containing from 4 to 8 carbon atoms or a heterocyclic group;
R² and R³ which may be the same or different represent a hydrogen atom or an alkyl group;
R⁴ represents a hydrogen atom or an alkyl group which alkyl group may be substituted by an aryl or aryloxy group which aryl group or aryloxy group may be substituted by an alkoxy ($C_{1-4}$) substituent, or R⁴ may represent an aryl group which may be substituted by an alkoxy ($C_{1-4}$) substituent; and X represents a pharmaceutically acceptable anion of an inorganic or organic acid. These compounds have therapeutic utility particularly improving glucose utilization.

13 Claims, No Drawings

ISOQUINOLIUM COMPOUNDS FOR TREATING DIABETES

This is a continuation of application Ser. No. 405,120, filed Oct. 10, 1973, now abandoned.

This invention relates to novel isoquinoline derivatives, to a process for the preparation thereof, to pharmaceutical compositions containing such compounds, and to their use in therapy.

We have found that the compounds of the invention alter the pattern of the metabolism of glucose so that the rates of its breakdown and re-synthesis is increased and the body tissues become more effective in using it. This biochemical profile is similar to that of biguanides such as phenformin that are anti-hyperglycaemic agents used in the treatment of diabetes, especially in cases of the maturity-onset type. The compounds of the invention, however, lack many of the cardiovascular and other side-effects of the biguanides and may thus be improved therapeutic agents.

The present invention provides compounds of the general formula I:

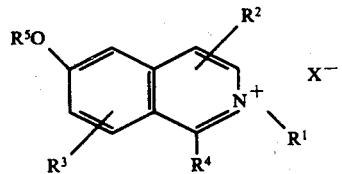

(I)

in which $R^1$ and $R^5$, which may be the same or different, represent an alkyl, alkenyl or alkynyl group, which groups may optionally be substituted by an amino, alkylamino or dialkylamino groups or by hydroxy, alkoxy ($C_{1-4}$) aroyl, (preferably benzoyl), aryl (preferably phenyl) or aryloxy (preferably phenoxy) groups where the aroyl, aryl or aryloxy groups may contain in additional alkoxy ($C_{1-4}$) substituent; or $R^5$ represents a cycloalkyl group containing 4 to 8 carbon atoms (preferably cyclopentyl) or a heterocyclic group (preferably tetrahydrofuranyl). $R^2$ and $R^3$ may be the same or different and represent a hydrogen atom or an alkyl group. $R^4$ represents a hydrogen atom or an alkyl group which may be substituted by an aryl or aryloxy group which aryl group or aryloxy group may be substituted by an alkoxy ($C_{1-4}$) substituent or $R^4$ may represent an aryl group, which may be substituted by an alkoxy ($C_{1-4}$) substituent. X represents a pharmaceutically acceptable anion of an inorganic or organic acid e.g. chloride, bromide, iodide, sulphate, hydrogen sulphate, sulphonate, methosulphate, ethosulphate or acetate.

When used above the term alkyl means a straight or branched chain alkyl group preferably containing 1 to 6 carbon atoms and the terms alkenyl and alkynyl refer to straight or branched chain alkenyl and alkynyl groups, preferably containing 2 to 6 carbon atoms.

A preferred class of compounds according to the invention is that in which $R^1$ represents alkyl ($C_{1-4}$), preferably methyl, ethyl, isopropyl or butyl; aminoalkyl, preferably aminoethyl and dialkylaminoalkyl, preferably dimethylaminoethyl; alkoxyalkyl, preferably 2-ethoxyethyl, alkenyl, preferably allyl; alkynyl, preferably propynyl, aralkyl, preferably benzyl or p-methoxybenzyl, aryloxyalkyl, preferably phenoxyethyl; aroylalkyl, preferably phenacyl or 4-methoxyphenacyl. $R^2$ represents hydrogen or alkyl ($C_{1-4}$) preferably methyl. $R^3$ represents hydrogen. $R^4$ represents hydrogen, alkyl, preferably methyl or ethyl; aralkyl, preferably benzyl; aryl, preferably p-methoxyphenyl. $R^5$ represents alkyl ($C_{1-5}$), preferably methyl ethyl, isopropyl, pentyl or isopentyl, aminoalkyl, preferably 2-aminoethyl, hydroxyalkyl, preferably 2-hydroxyethyl, alkoxyalkyl, preferably 2-ethoxyethyl, 2-methoxyethyl, 3-methoxypropyl or ethoxymethyl, alkenyl, preferably allyl or dimethylallyl, cycloalkyl, preferably cyclopentyl, aralkyl, preferably benzyl, aryloxyalkyl, preferably phenoxyethyl, or a heterocyclic group, preferably 3-tetrahydrofuranyl. X represents iodide, bromide, chloride, toluene sulphonate or hydrogen sulphate.

Using the test procedure described by A. Dunn et al, Biochemistry, 6, 6, 1967, the compounds of the invention have been shown to increase the rate of utilisation and recycling of glucose in rats and dogs.

The compound was administered orally to the rat or dog and a mixture of glucose-6-H3 and glucose-6-C14 with a H3:C14 ratio of 10:1 injected intravenously. The specific activity with respect to H3 and C14 of the plasma glucose was subsequently measured, and the results expressed as percentage increases of utilisation and recycling of glucose.

In the above tests our compounds were found to have a potency similar to, or greater than that of the biguanide phenformin as shown by the results in the table.

| | Rat | | | Dog | |
|---|---|---|---|---|---|
| Compound of | % increase in glucose utilisation | % increase in glucose recycling. | Dose mg/kg | % increase in glucose utilisation | Dose mg/kg |
| Example 1(b) | 80 | 150 | 20 | 50 | 2 |
| Example 9(b) | 81 | 71 | 10 | 50 | 1 |
| Example 9(e) | 50 | 40 | 10 | 60 | 8 |
| Phenformin | 60 | 52 | 20 | 50 | 7.5 |

The compounds of the general formula I may be prepared by the following route:

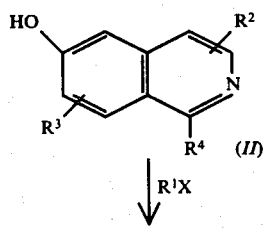

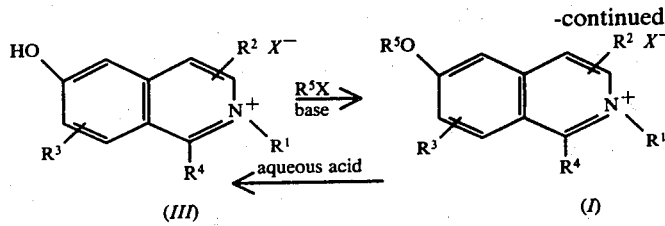

(in which $R^1$–$R^5$ and X have the meanings given above or are groups convertible thereto).

In this process the hydroxyisoquinoline II is converted into the hydroxyisoquinolinium compound III by treatment with a conventional alkylating agent ($R^1X$) e.g. a halide, sulphate or sulphonate ester. The reaction may advantageously be carried out at room temperature or above, and with or without a solvent, e.g. an aliphatic alcohol, a polar aprotic solvent, e.g. acetone, butanone or acetonitrile, or a non-polar solvent, e.g. benzene or toluene. The reaction can be carried out conveniently at reflux in the solvent concerned.

The compounds of the invention are obtained from the corresponding hydroxyisoquinolinium compounds III by treatment with conventional alkylating agents ($R^5X$) e.g. halides, sulphates, sulphonate esters etc. in the presence of an inorganic base e.g. sodium or potassium carbonate. The reactions may advantageously be carried out at room temperature or above, in a polar solvent e.g. an aliphatic alcohol, acetonitrile, dimethylformamide etc. The use of acetonitrile is particularly advantageous.

The starting hydroxyisoquinolines II are either known compounds or may be prepared by the standard processes of isoquinoline chemistry.

Thus, the invention provides a process for the preparation of compounds according to the invention which comprises alkylating a compound of formula (III). The compound (III) may be made from (II) as explained above.

Compounds according to the invention may also be converted into other such compounds. For example hydrolysis of a group $R^5$ with a suitable aqueous acid e.g. hydrobromic acid, and subsequent re-alkylation of the corresponding hydroxyisoquinolinium (III) provides a compound in which the group $R^5$ has one of the other meanings possible. Another possibility consists in converting the group $R^1$ into another group having one of the other meanings possible, for example when $R^1$ represents an aminoethyl group it may be converted to a dimethylaminoethyl group by treatment with formic acid and formaldehyde.

In a modification of the process the ether (IV) is quaternised with a suitable alkylating agent $R^1X$ to give compounds (I)

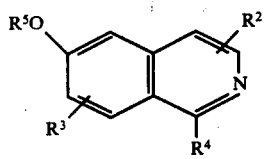

(IV)

This modification is particularly useful since isoquinolines (IV) where $R^5$ = Alkyl (e.g. Me) are especially accessible by conventional methods, and the resulting quaternary salts (I) ($R^5$ = Alkyl) can be hydrolysed and re-alkylated to provide compounds in which $R^5$ has one of the other meanings already given. The reaction conditions for this modification are preferably the same as those used for the preparation of the isoquinolinium compound III from the hydroxyisoquinoline II.

The hydroxy and alkoxyisoquinolines (II) and (IV) may be synthesised by standard processes of isoquinoline chemistry; one particularly useful route is outlined below:

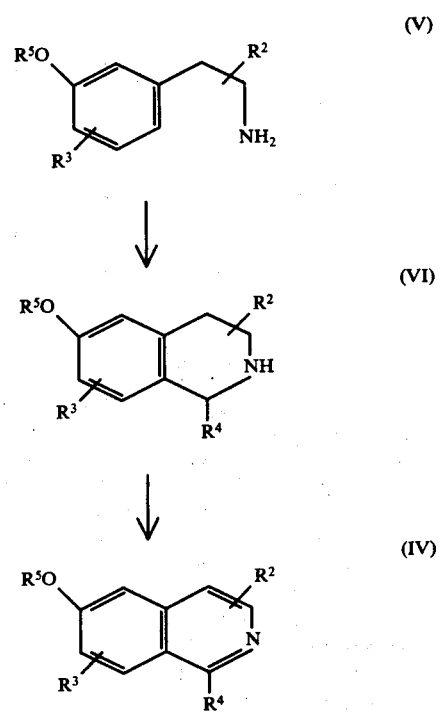

The phenethylamine (V) may be converted into the tetrahydroisoquinoline (VI) by a Pietet-Spengler reaction, or by a Bischler-Napieralski reaction followed by reduction of the resulting 3,4-dihydroisoquiniline. Dehydrogenation of (VI), for example by heating with Pd-C catalyst at high temperatures in p-cymene, gives the required alkoxyisoquinoline (IV). Although the above reaction scheme may be carried out when $R^5$ = H, it is often more desirable to prepare the hydroxyisoquinoline (II) by acid hydrolysis of the ether (IV) particularly when $R^5$ = methyl or ethyl.

The term alkylating agent as used herein in relation to the compounds $R^1X$ and $R^5X$ is not to be construed as limiting the groups $R^1$ and $R^5$ to alkyl groups. The term is merely a convenient and conventional way of describing the compound $R^1X$ and $R^5X$ in which $R^1$ and $R^5$ have the definitions given herein.

The invention also provides pharmaceutical compositions which contain an isoquinoline derivative according to the invention in association with a pharmaceutically acceptable carrier.

The pharmaceutical compositions according to the invention, may be formulated for use in the conventional manner with the aid of carriers or excipients and formulatory agents as required and with or without supplementary medicinal agents.

Oral administration is most convenient in the form of tablets which may or may not be coated, capsules, pastes, aqueous or oily suspensions, solutions or emulsions. Carriers include inert diluents such as calcium sulphate or calcium phosphate and/or disintegrating agents such as starch or alginic acid. Magnesium stearate may be used as a lubricating agent. For liquid oral formulations suspending agents such as sodium carboxy methyl cellulose may be used together with preservatives and flavouring or sweetening agents such as sucrose, dextrose and glycerol.

Injections may be formulated with the aid of physiologically acceptable carriers and agents as solutions, suspensions or as dry products for reconstruction before use.

The dosage at which the active ingredient is administered may vary within a wide range. A suitable oral dosage range is generally from 5 - 500 mg daily. The pharmaceutical composition may, with advantage, be formulated to provide a dose within these ranges either as a single unit or as a number of units.

The following Examples illustrate the invention. In these Examples, Example 8 describes the production of a starting material for Examples 9-11. All temperatures are given in degrees centigrade.

EXAMPLE 1 a. 2-Benzyl-6-methoxyisoquinolinium bromide

6-Methoxyisoquinoline (1.6 g) and benzyl bromide (2 ml) in acetone (75 ml) were heated under reflux for 1 hour. The mixture was diluted with ether and cooled to 0°. The solid was filtered off and recrystallised from methanol/ether, and had m.p. 155°-158°.

The following compounds were prepared by a similar procedure. (The reaction time is shown in brackets):

b. 6-Methoxy-2-methylisoquinolinium iodide, m.p. 232°-234° (½ hr.).

c. 6-Methoxy-2,3-dimethylisoquinolinium iodide, m.p. 231°-233° (2 hr.).

d. 6-Methoxy-2-(4-methoxybenzyl)isoquinolinium chloride sesquihydrate, m.p. 80°-83° (24 hr.).

e. 6-Methoxy-2-phenacylisoquinolinium bromide, m.p. 211° (1 hr.).

f. 1-Benzyl-6-methoxy-2-methylisoquinolinium iodide monohydrate, m.p. 166°-168° (5 hr.).

g. 6-Methoxy-1,2-dimethylisoquinolinium iodide, m.p. 243°-245° (1 hr.).

h. 6-Methoxy-1-(4-methoxyphenyl)-2-methylisoquinolinium chloride, m.p. 207°-209° (6 hr.).

i. 1-Ethyl-6-methoxy-2,3-dimethylisoquinolinium iodide, m.p. 251°-252° (24 hr.).

j. 6-Methoxy-2-(4-methoxyphenacyl)isoquinolinium bromide, m.p. 208°-210° (1 hr.).

EXAMPLE 2 a. 6-Ethoxy-2-butylisoquinolinium iodide

6-Ethoxyisoquinoline (0.5 g.), and butyl iodide (0.5 g.) in acetonitrile (50 ml) were heated under reflux for 24 hours. The solution was cooled and diluted with ether to give pale yellow crystals, m.p. 129°.

The following compounds were prepared by a similar procedure. (The reaction time is shown in brackets):

b. 6-Ethoxy-2-isopropylisoquinolinium iodide, m.p. 137° (10 hr.).

c. 2-Allyl-6-methoxyisoquinolinium bromide, m.p. 140°-142° (48 hr.).

d. 2-(2-Ethoxyethyl)-6-methoxyisoquinolinium chloride sesquihydrate, m.p. 57° (72 hr.).

e. 6-Ethoxy-2-(2-hydroxyethyl)isoquinolinium bromide, m.p. 115°-166° (48 hr.).

EXAMPLE 3

6-Ethoxy-2-(2-phenoxyethyl)isoquinolinium pierate

6-Ethoxyisoquinoline (0.5 g.), 2-phenoxyethyl bromide (0.66 g.) and sodium iodide (0.2 g.) in acetonitrile (50 ml) were heated under reflux for 4 days. The mixture was evaporated to dryness, the residue dissolved in ethanol (5 ml), and pieric acid (1 g.) in ethanol (5 ml) was added. The yellow precipitate was filtered off and recrystallised from acetone, and had m.p. 149°-152°.

EXAMPLE 4

6-Ethoxy-2-(2-propynyl)isoquinolinium iodide

6-Ethoxyisoquinoline (500 mg.), propargyl bromide (500 mg.) and sodium iodide (300 mg.) were heated under reflux in acetonitrile (30 ml) for 5 hrs. The mixture was evaporated to dryness, the residue taken up in hot water (5 ml) and a saturated aqueous solution (5 ml) of sodium iodide added to the cooled filtrate. The solid that precipitated was recrystallised from isopropanol/ether, m.p. 121°-123°.

EXAMPLE 5

6-Ethoxy-2-ethylisoquinolinium hydrogen sulphate, monohydrate

6-Ethoxyisoquinoline (0.5 g.) and ethyl sulphate (0.6 g.) in moist acetonitrile (50 ml.) were heated under reflux for 4 hours. The mixture was cooled, ether was added and the white solid was collected and crystallised from acetonitrile and had m.p. 63°.

EXAMPLE 6

2-(2-Aminoethyl)-6-ethoxyisoquinolinium bromide hydrobromide

6-Ethoxyisoquinoline (0.5 g.) and ethyl (2-bromoethyl) carbamate (0.7 g.) in acetonitrile (20 ml) were heated under reflux for 50 hrs. The solvent was removed in vacuo and the residue triturated with ethyl acetate to give 2-(2-carbethoxyaminoethyl)-6-ethoxyisoquinolinium bromide (1.0 g.). The crude bromide was heated under reflux in 24% aqueous hydrobromic acid (16 ml) for 2 hrs. The solvent was removed in vacuo and the residue was crystallised from ethanol and had m.p. 238°-240° (dec.).

EXAMPLE 7

2-(2-Dimethylaminoethyl)-6-ethoxyisoquinolinium bromide, hydrobromide, monohydrate 2-(2-Aminoethyl)-6-ethoxyisoquinolinium bromide (0.15 g.), formic acid (2 ml) and formaldehyde (2 ml, 35% aqueous solution) were heated for 6 hr. on a steam bath. The solution was evaporated and the residue was treated with hydrobromic acid (0.5 ml 48%). The solution was evaporated and the residue crystallised from ethanol to give a white solid m.p. 233°-235°.

EXAMPLE 8

6-Hydroxy-2-methylisoquinolinium bromide

Method (a) 6-Methoxy-2-methylisoquinolinium iodide (7.3 g., Example 1) in 48% hydrobromic acid (70 ml) was heated under reflux for 24 hours. The solvent was removed in vacuo to give a solid that we recrystallised from ethanol/ethyl acetate and had m.p. 216°–219°.

Method (b) Methyl iodide (4 ml) and 6-hydroxyisoquinoline (1 g.) in acetone (50 ml) and methanol (20 ml) were heated under reflux for 2 hours. The solution was cooled and diluted with ether to give the quaternary iodide as colourless crystals, m.p. 202°–204°. The iodide was converted into the bromide, m.p. 216°–219°, by heating under reflux with 48% hydrobromic acid for 24 hours, evaporating the mixture and crystallising the residue from a mixture of ethanol and ethyl acetate.

EXAMPLE 9 a. 6-Benzyloxy-2-methylisoquinolinium bromide

Sodium carbonate (5 g.), benzyl bromide (2 ml), 6-hydroxy-2-methylisoquinolinium bromide (2.5 g.) in acetonitrile (100 ml) were heated under reflux for 2 hr. The suspension was filtered hot and the filtrate was diluted with ether. The solid that precipitated was crystallised from acetonitrile, and had m.p. 210°–213°.

The following compounds were prepared by a similar procedure. (The reaction time is shown in brackets):

a. 6-Ethoxy-2-methylisoquinolinium bromide monohydrate, m.p. 130°–133° (2 hr.).

c. 6-(2-Hydroxyethoxy)-2-methyolisoquinolinium bromiade, m.p. 194°–196° (6 hr.).

d. 6-Allyloxy-2-methylisoquinolinium bromide monohydrate, m.p. 112°–115° (3 hr.).

e. 6-Isopropoxy-2-methylisoquinolinium iodide, m.p. 206°–208° (6 hr.).

f. 6-(2-Ethoxyethoxy)-2-methylisoquinolinium bromide monohydrate, m.p. 83°–85° (48 hr.).

g. 2-Methyl-6-pentyloxyisoquinolinium bromide monohydrate, m.p. 105°–107° (16 hr.).

h. 2-Methyl-6-(3-methylbut-2-enyloxy)isoquinolinium bromide hydrate, m.p. 77° (20 hr.).

i. 6-(2-Methoxyethoxy)-2-methylisoquinolinium chloride monohydrate, m.p. 64°–65° (35 hr.).

j. 6-(3-Methoxypropoxy)-2-methylisoquinolinium chloride monohydrate, m.p. 83°–85° (24 hr.).

k. 6-Ethoxymethoxy-2-methylisoquinolinium chloride, m.p. 125°–128° (1 hr.).

l. 2-Methyl-6-(2-phenoxyethoxy)isoquinolinium bromide, m.p. 223°–225° (42 hr.).

m. 6-Cyclopentyloxy-2-methylisoquinolinium bromide monohydrate, m.p. 178°–80° (26 hr.).

n. 6-Ethoxy-2,3-dimethylisoquinolinium bromide monohydrate, m.p. 214°–216° (4½ hr.).

o. 6-(2-Ethoxyethoxy)-2,3-dimethylisoquinolinium bromide monohydrate, m.p. 177°–180° (76 hr.).

p. 2-Methyl-6-(2-propynyloxy)isoquinolinium bromide, m.p. 207° (d) (4 hr.).

EXAMPLE 10

6[3-Tetrahydrofuranyloxy]-2-methylisoquinolinium-p-toluenesulphonate

6-Hydroxy-2-methylisoquinolinium bromide (2.4 g.), sodium carbonate (5 g.) and 3-hydroxytetrahydrofuran, p-toluenesulphonate (5 g.) in acetonitrile (100 ml) were heated under reflux for 60 hours. The mixture was cooled and diluted with ether. The solid that crystallised was collected and had m.p. 144°–146°.

EXAMPLE 11

6-(2-Aminoethoxy)-2-methylisoquinolinium bromide 1. 2-Methyl-6(2-Phthalimidoethoxy)isoquinolinium bromide 6-Hydroxy-2-methylisoquinolinium bromide (2.4 g.), sodium carbonate (5 g.) and phthalimidoethyl bromide (2.6 g.) in acetonitrile (100 ml) were heated under reflux for 9 days. The mixture was filtered hot and the filtrate evaporated to give an oily solid. It was washed with chloroform, and light petroleum ether (b.p. 40°–60°) was added to give an oil that solidified on trituration, m.p. 165°–169°.

2. 6-(2-Aminoethoxy)-2-methylisoquinolinium bromide

2-Methyl-6(2-Phthalimidoethoxy)isoquinolinium bromide (900 mg.) and hydrazine hydrate (0.3 g.) in ethanol (50 ml) were heated under reflux for 2 hr. The mixture was cooled and the precipitated hydrazide filtered off. Addition of ether to the filtrate gave a solid which was recrystallised from acetonitrile and had m.p. 173°–176°.

EXAMPLE 12

Pharmaceutical Compositions

In these Examples the compound identified as AH 10713 is the compound of Example 9(c). It may be replaced by any other compound according to the invention.

Tablets

To prepare 10,000 tablets, each containing 50 mg AH 10713

Mix together 500 g. of powdered AH 10713 with 1500 g. of lactose and 200 g. of maize starch. Thoroughly mix with a sufficient quantity of a hot 10% aqueous starch paste to produce a uniform moist mass. Granulate the mass by passing through a No. 8 B.S.S. sieve and dry at 50° C in a fluidised bed dryer. Blend the granules with 11.5 g. of magnesium stearate and sufficient dried maize starch to give a total batchweight of 2.30 kg. Compress the granules in a suitable tabletting press so that each tablet weighs 230 mg. and is 8.5 mm in diameter.

To prepare 10,000 tablets, each containing 25 mg AH 10713

Mix together 250 g. of powdered AH 10713, 200 g. of microcrystalline cellulose, 1.00 kg of spray-dried calcium phosphate dihydrate sold under the trade name "Encompress" then blend with 7.25 g. of magnesium stearate. Compress the mixed powder on a tabletting press to give tablets each weighing 146 mg. and of 6.5 mm diameter.

Capsules

To prepare hard gelatin capsules each containing 25 mg or 50 mg of AH 10713

Mix the required quantity of drug with sufficient microcrystalline cellulose containing 0.5% of magnesium stearate to enable an adequate fill to be obtained in a No. 2 size hard gelatin capsule to give the dose desired.

Oral Syrup

Prepare an aqueous solution of the drug containing 0.5% hydroxyethyl cellulose. Adjust the volume with syrup so that each 5 ml contains 25 mg AH 10713. The syrup contains suitable sweetening, flavouring and buffering agents and is preserved with a mixture of alkyl-parahydroxybenzoates.

We claim:

1. A method of treatment of diabetes which comprises administering to a patient an effective amount of a compound of the formula:

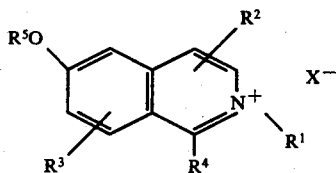

in which $R^1$ represents $C_{1-4}$ alkyl; aminoethyl; dimethylaminoethyl; 2-ethoxyethyl; allyl; propynyl; benzyl, p-methoxybenzyl; phenoxyethyl; phenacyl or 4-methoxyphenacyl; $R^2$ represents hydrogen or $C_{1-4}$ alkyl; $R^3$ represents hydrogen; $R^4$ represents hydrogen; methyl, ethyl; benzyl; or p-methoxyphenyl; $R^5$ represents $C_{1-5}$ alkyl; 2-aminoethyl; 2-hydroxyethyl; 2-ethoxyethyl, 2-methoxyethyl, 3-methoxypropyl, ethoxymethyl; allyl, dimethylallyl; cyclopentyl; benzyl; phenoxyethyl or 3-tetrahydrofuranyl; X represents iodide, bromide, chloride, toluene sulphonate or hydrogen sulphate.

2. The method of claim 1 wherein $R^1$ represents methyl, ethyl, isopropyl or butyl; and $R^5$ represents methyl, ethyl, isopropyl, pentyl or isopentyl.

3. The method of claim 1 wherein the compound is 6-(2-ethoxyethoxy)-2-methylisoquinolinium bromide monohydrate.

4. A method of treatment of diabetes which comprises administering to a patient an effective amount of 6-ethoxy-2-(2-hydroxyethyl)isoquinolinium bromide.

5. The method of claim 1 wherein the compound is administered orally.

6. The method of claim 5 wherein the effective amount of the compound is in a dosage range of from 5–500 mg daily.

7. The method of claim 1 wherein the compound is 6-methoxy-2-methylisoquinolinium iodide.

8. The method of claim 1 wherein the compound is 6-methoxy-2,3-dimethylisoquinolinium iodide.

9. The method of claim 1 wherein the compound is 6-methoxy-1,2-dimethylisoquinolinium iodide.

10. The method of claim 1 wherein the compound is 6-ethoxy-2-butylisoquinolinium iodide.

11. The method of claim 1 wherein the compound is 6-ethoxy-2-ethylisoquinolinium hydrogen sulphate, monohydrate.

12. The method of claim 1 wherein the compound is 6-ethoxy-2-methylisoquinolinium bromide monohydrate.

13. The method of claim 1 wherein the compound is 6-ethoxy-2,3-dimethylisoquinolinium bromide monohydrate.